United States Patent [19]
Gonon

[11] Patent Number: 6,066,150
[45] Date of Patent: May 23, 2000

[54] SURGICAL DISSECTION INSTRUMENT USING A HIGH-PRESSURE LIQUID JET

[75] Inventor: Bertrand Gonon, Lyons, France

[73] Assignee: Saphir Medical S.A., Lyons, France

[21] Appl. No.: 09/011,461

[22] PCT Filed: Jul. 23, 1996

[86] PCT No.: PCT/FR96/01154
§ 371 Date: Jan. 22, 1998
§ 102(e) Date: Jan. 22, 1998

[87] PCT Pub. No.: WO97/03713
PCT Pub. Date: Feb. 6, 1997

[30] Foreign Application Priority Data

Jul. 24, 1995 [FR] France ................................. 95 09127

[51] Int. Cl.[7] .................................................. A61B 17/32
[52] U.S. Cl. ............................................. 606/167; 604/22
[58] Field of Search ................................. 604/19, 22, 30, 604/35; 606/1, 110, 127, 159, 167, 170, 185

[56] References Cited

U.S. PATENT DOCUMENTS

| | | |
|---|---|---|
| 3,713,443 | 1/1973 | Fertik . |
| 4,519,385 | 5/1985 | Atkinson . |
| 5,147,292 | 9/1992 | Kullas et al. . |
| 5,191,881 | 3/1993 | Beck . |
| 5,254,083 | 10/1993 | Gentelia et al. ........................... 604/34 |
| 5,254,117 | 10/1993 | Rigby et al. . |
| 5,336,170 | 8/1994 | Salerno et al. ........................... 606/190 |
| 5,496,267 | 3/1996 | Drasler et al. ........................... 606/159 |
| 5,643,299 | 7/1997 | Bair ......................................... 606/166 |

FOREIGN PATENT DOCUMENTS

| | | |
|---|---|---|
| 0 411 170 | 2/1991 | European Pat. Off. . |
| 93 03777 | 3/1993 | WIPO . |

Primary Examiner—Glenn K. Dawson
Attorney, Agent, or Firm—Davis and Bujold

[57] ABSTRACT

A surgical dissection instrument using a high-pressure liquid jet including a handpiece provided with a mechanism for generating and controlling the liquid jet. The handpiece has a simple design and is cheap to manufacture and may thus be a single-use handpiece. The handpiece is ergonomically shaped and may be held in one hand with all the function controls being operated by the fingers of the same hand. The instrument has a mechanism provided with a flexible tubing (13) for supplying the high-pressure liquid to the handpiece (10). The handpiece (10) has a squeezing mechanism for locally and momentarily closing off the flexible tubing (13) to cut off the supply of liquid: the mechanism consists of a moveable squeezing projection (25) on a hinged control handle (17), and a stationary squeezing projection (26) secured to the body (15) of the handpiece (10). The handpiece (10) has a mechanism (18) for locking the control handle (17) and cutting off the liquid jet.

12 Claims, 4 Drawing Sheets

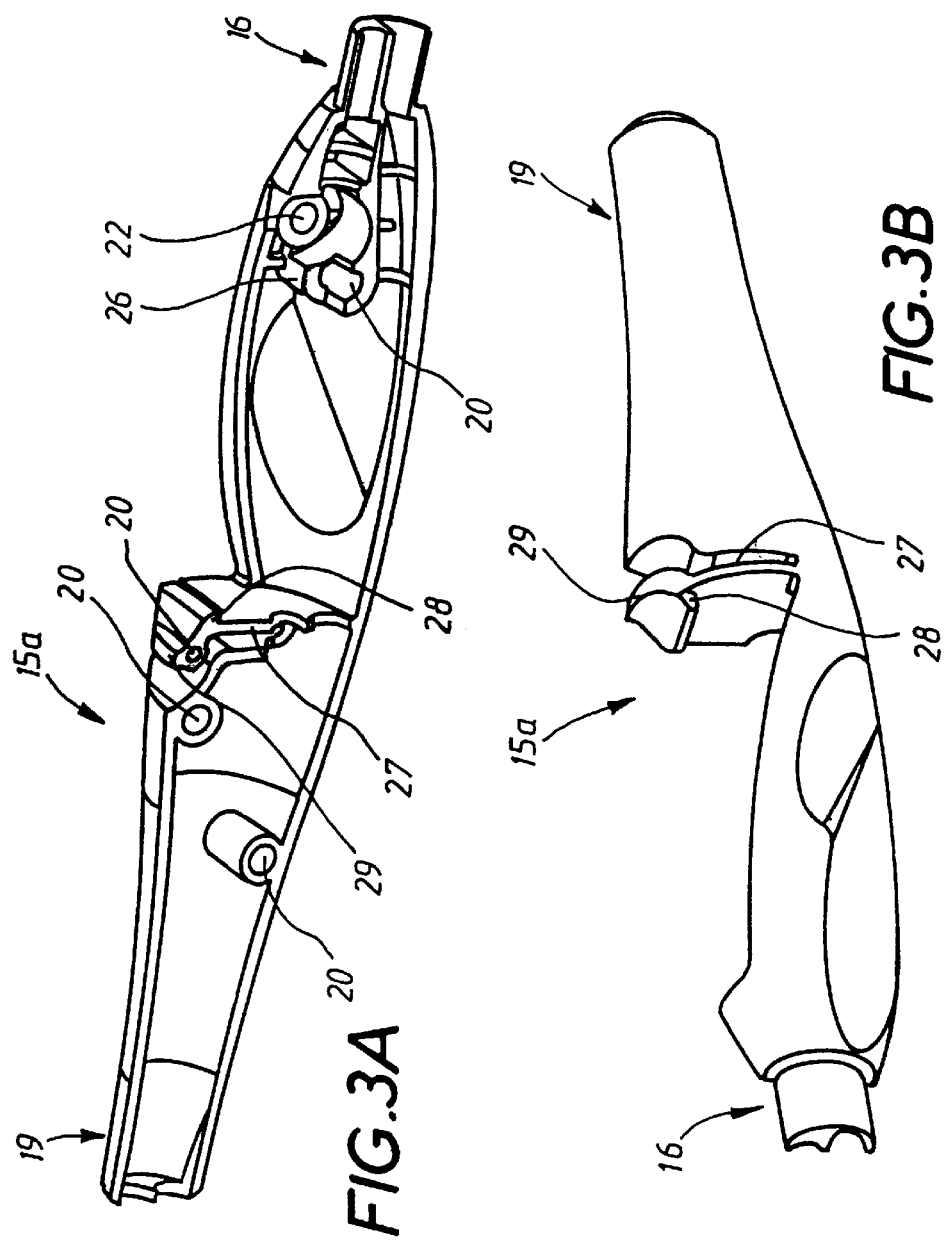

SURGICAL DISSECTION INSTRUMENT USING A HIGH-PRESSURE LIQUID JET

The present invention relates to a surgical dissection instrument using a high-pressure liquid jet, also called a lancet, comprising a handpiece provided with means of generating and controlling a fine jet of said liquid, notably made up of physiological salt solution, and a device for supplying said handpiece with this high-pressure liquid.

BACKGROUND OF THE INVENTION

There are numerous known instruments of this type called lancets using a liquid jet. One of these instruments is for example described in the European publication No. 0 303 557 A3. The hand-operated instrument is equipped with a a manual control valve which is used to stop the pressurized flow of liquid during an operation. These valves are usually of complex construction due to the fact that they comprise at least one moving piece and a release spring designed to bring the moving piece back to its initial position. Due to this relative complexity, the handpiece becomes a costly piece which does not lend itself to being used once. However, the sterilisation requirements which are imposed on this type of instrument, and the problems posed when reusing it, particularly as regards the risks of contagion, make it virtually obligatory to use it once only.

Handpieces to be used only once already exist and are used in devices for irrigating and washing cuts, being supplied with a low-pressure or even air pressure liquid. Such handpieces are described for example in the American publications U.S. Pat. No. 4,519,385 and U.S. Pat. No. 5,147,292. Their design is completely incompatible with the technical constraints imposed in an instrument designed to dissect tissues and in which the pressure of the liquid can reach 70 bar.

Furthermore, the handpiece must have a ergonomic shape, fit in one hand and have all the function controls which can be operated easily using this hand's fingers. It must be possible to control it with one hand wearing a surgeon's glove, without the glove being subjected to constraints which might injure it. Furthermore, the fingers must be able to control the partial or total opening and closing of the jet of pressurised liquid instantaneously, quite effortlessly. The control manoeuvre has to be very flexible and quick given the precision requirements linked to the use of a lancet.

The main function of the handpiece is to control the supply and stop the supply of high-pressure liquid.

One advantageous secondary function is locking the liquid supply control in the stop position.

Finally, a third function is the suction function.

SUMMARY OF THE INVENTION

The surgical dissection instrument using a high-pressure liquid jet according to the invention, which overcomes the drawbacks of prior art and which offers an efficient and inexpensive way of fulfilling the main function, consisting in opening and stopping the liquid supply, is characterized in that:

the handpiece comprises a hollow body of generally elongated shape, this body extending from a near end-cap to a far end-cap, both ends being located significantly on the same axis, said device to supply the handpiece comprises a flexible tube housed in said body and extending from the far end-cap up to the near end-cap in a significantly rectilinear manner, said tube being designed to withstand a high pressure of at least 40 to 70 bar.

the near end-cap comprises a nozzle designed to generate said liquid jet, said means of generating and controlling said high-pressure liquid jet comprise:

pinching means, designed to locally squash said tube so as to stop said high-pressure liquid jet and comprising, in an area close to the near end-cap, a fixed squeezing projection secured to said body, supporting said tube and arranged perpendicular to the latter, and a movable squeezing projection arranged opposite said fixed projection on the other side of said tube perpendicular to the latter, the two projections defining between them a space for said tube to pass, the movable projection being designed to move in relation to the fixed projection so as to reduce said space until it is cancelled, thus ensuring that said tube is fully squashed in a significantly perpendicular direction to the latter, a lever for controlling said pinching means designed to be hand-operated by a user, mounted in a corresponding housing located in the periphery of said body and articulating on a swivel pin in said body, this swivel pin being located between the near end-cap and the fixed squeezing projection, the control lever being provided with the said movable squeezing projection.

locking means combined with said control lever and designed, in the locked position, to block said control lever in a low position in which the tube is squashed between the two squeezing projections and the high-pressure liquid jet is cut off, and in the unlocked position, to release this lever which rises into a high position under the effect of the high-pressure liquid jet which opens the tube.

According to a preferred embodiment, the handpiece is made of an injection-moulded thermoplastic synthetic material and the body is made up of two half shells assembled by slotting them together. This construction has the advantage of being very economical and makes it possible to make pieces to be used once only, which are therefore disposable.

In an advantageous manner, said control lever has a generally rectangular shape and comprises a significantly flat or inwardly curved supporting area to receive the user's fingers or palm. More in particular, it is articulated on a pivot engaged in said half shells of the handpiece's body. Depending on its position, the space defined between the two squeezing projections is more or less confined.

In the preferred form of embodiment, the free end of said control lever defines with the pivot a lever arm D1 and the movable squeezing projection defines with said pivot a lever arm D2 smaller than D1, the ratio of the lever arms being at least between 4 and 6.

The locking means advantageously have a flexible tongue secured to the body and bearing a catch pin designed to cooperate with a grip secured to the control lever. Preferably, this flexible tongue comprises a pusher located at its upper end and designed to release said control lever.

According to the preferred form of embodiment, the instrument comprises a suction device, a flexible tube crossing said handpiece and a suction tube mounted in the near end-cap.

The handpiece advantageously comprises a chamber located between the end of the tube and the suction tube and at least one lateral opening provided in the wall of the handpiece which joins said chamber.

According to the preferred form of embodiment, the handpiece comprises two lateral openings corresponding to a central channel partially crossing said chamber, and a seal designed to seal either of said openings. This seal can have a cylindrical central part and two grooved lateral wings, its length being greater than the length of said handpiece.

Preferably, the nozzle and the suction tube are encompassed by protection cannula mounted on the near end-cap.

BRIEF DESCRIPTION OF THE DRAWINGS

The present invention shall be disclosed in more detail with reference to the description of a preferred form of embodiment given by way of an unrestricted example and illustrated by the attached drawings, in which:

FIGS. 3A and 3B show respectively inside and outside views of a constituent half shell of the handpiece.

DESCRIPTION OF THE PREFERRED EMBODIMENT(S)

Figure 1:
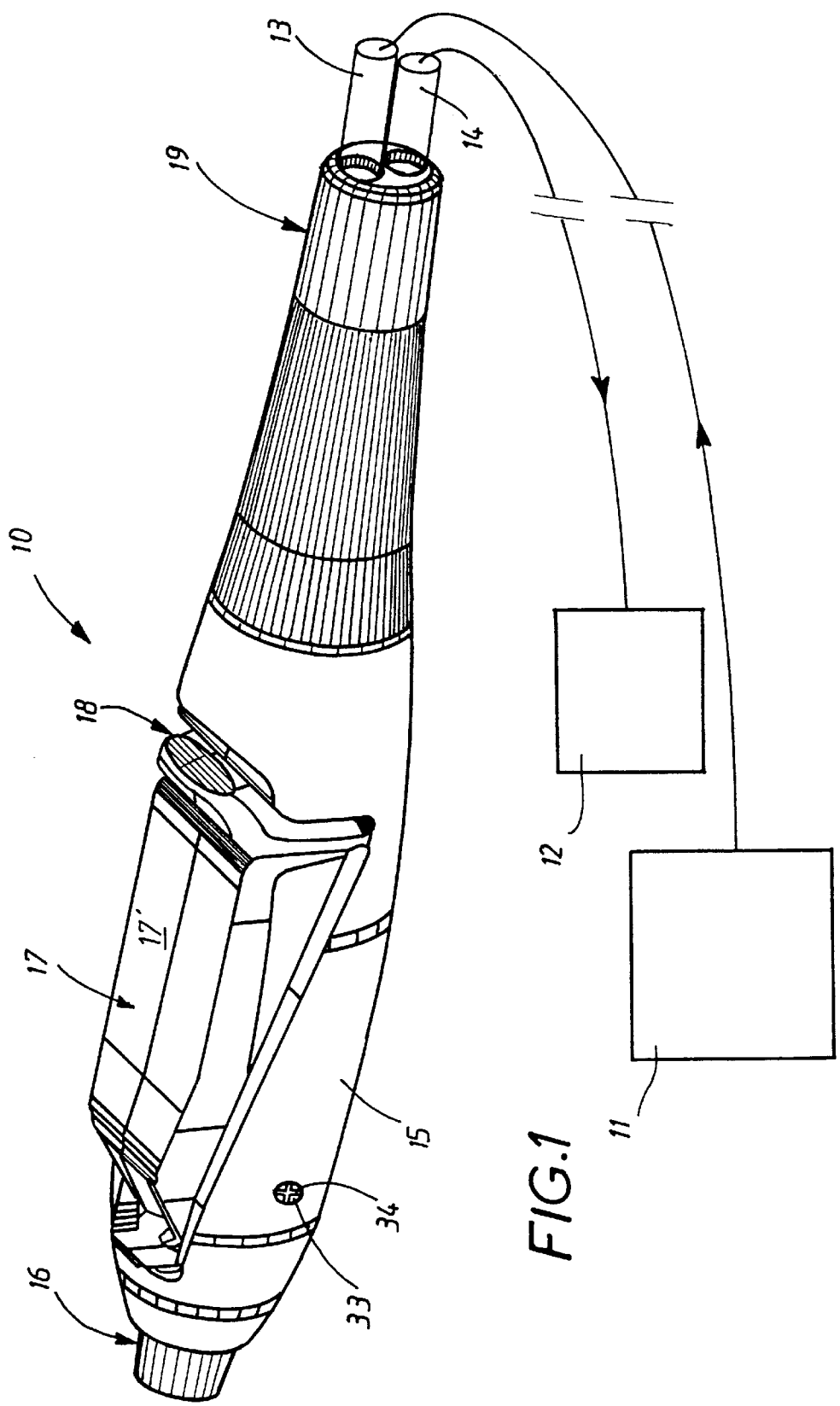
FIG. 1 shows a perspective of the hand-operated instrument, connected to its peripheral equipment shown schematically.
Figure 2:
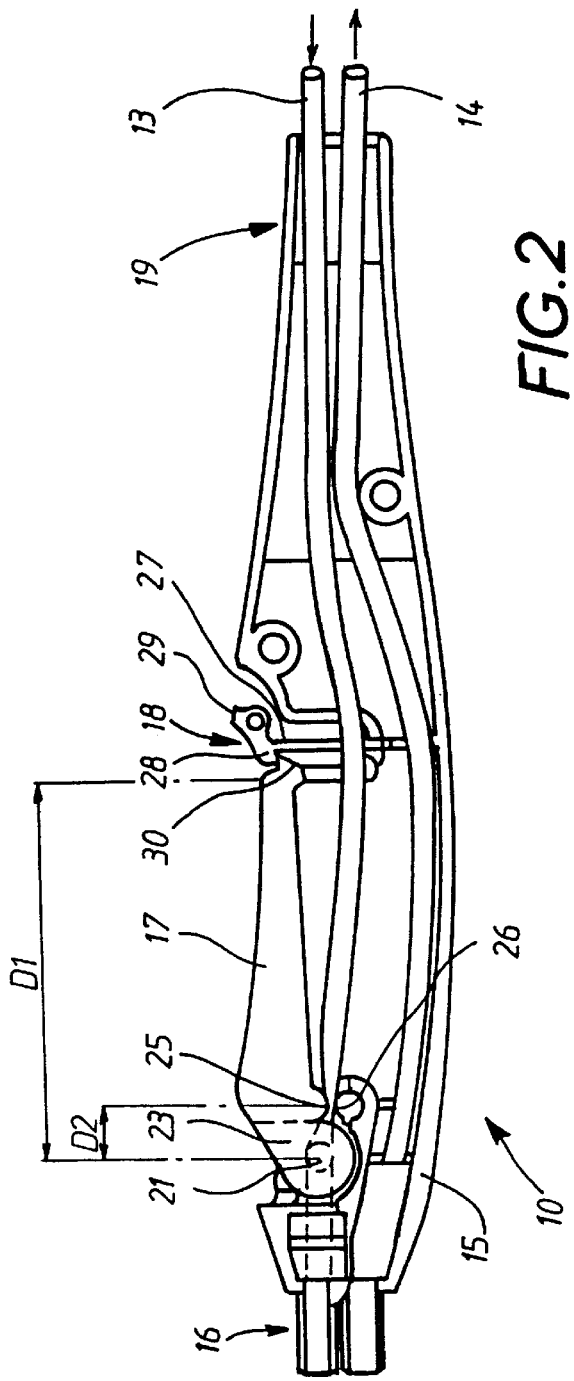
FIG. 2 shows an axial cutaway view of the hand-operated instrument according to the invention.
Figure 4:
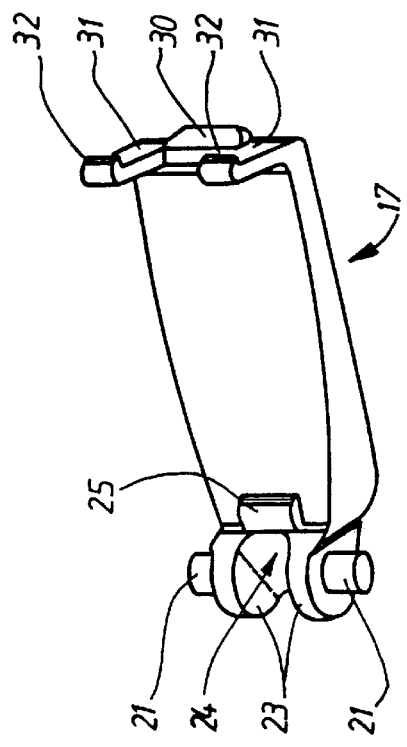
FIG. 4 shows a perspective of the handpiece's control lever.

With reference to the Figures, the surgical dissection instrument according to the invention comprises a handpiece 10, a source 11 for supplying a high-pressure physiological salt solution and a suction device 12. This peripheral equipment is connected to the handpiece by means of two flexible tubes respectively 13 and 14 partially shown on FIGS. 1, 2, 5A and 5B. These tubes offer the advantage of being reinforced by an armouring made of braided synthetic wires, so as to be able to withstand the pressure of the liquid which may reach 70 bar.

Figure 5A:
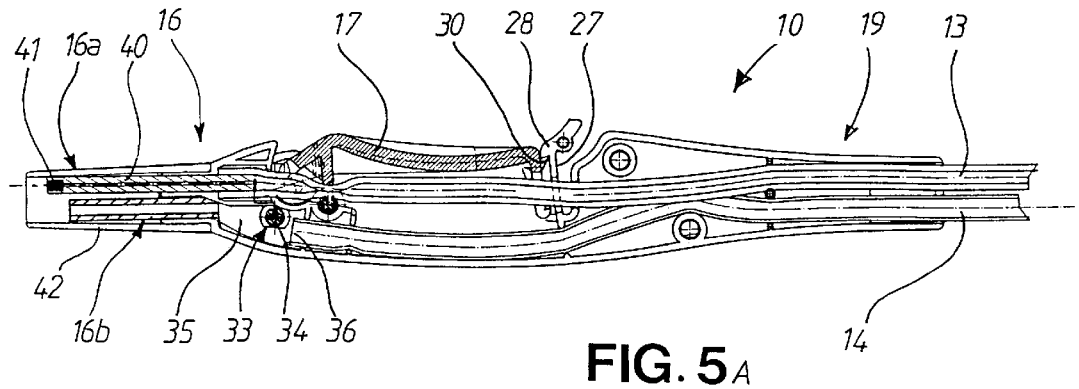
FIGS. 5A and 5B are axial cutaway views illustrating respectively the handpiece in the closing position and the opening position.
Figure 5B:
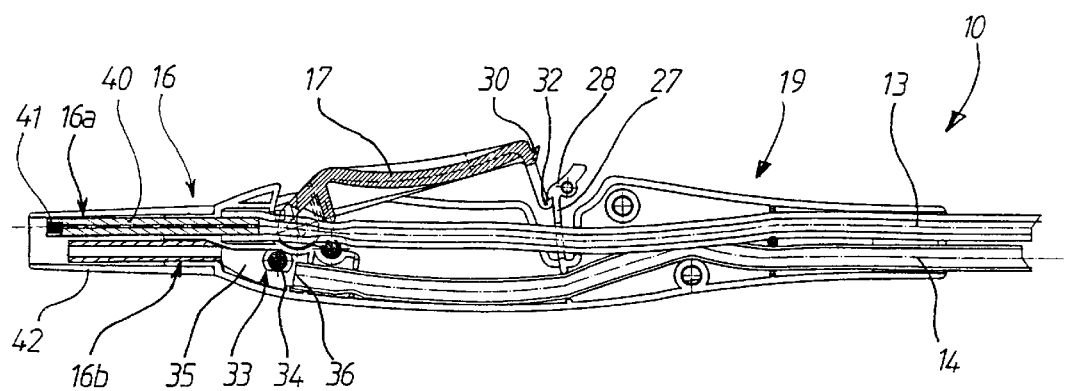

The handpiece 10 is of the disposable type, made entirely from injection-moulded thermoplastic synthetic material. It primarily comprises an ergonomic body 15 of generally elongated shape, with a significantly circular cross-section, this body extending from a near end-cap 16 to a far end-cap 19, both end-caps being significantly located on the same axis. With reference in particular to FIGS. 5A and 5B, the near end-cap 16 is designed to receive a nozzle 16a generating the jet of high-pressure liquid and arranged extending from the tube 13 and a suction tube 16b canalizing the suction and arranged extending from the tube 14. The nozzle 16a is made up of a rigid rod 40 inserted by one of its ends into the tube 13, crossed by a relatively narrow channel and provided at its other end with a sapphire needle with an approximately 0.1 mm orifice capable of generating a very fine jet of liquid. The nozzle 16a and the suction tube 16b are encompassed by a protection cannula 42 mounted on the near end-cap 16. The nozzle 16a is offset in relation to the free end of the cannula 42 and the suction tube 16b is offset in relation to the end of the nozzle 16a. The cannula 42 thus protects the elements which it encompasses but it also protects the close outside environment against possible splashes of liquid. It is preferably made of very flexible synthetic material to avoid injuring the tissues. This cannula 42 is significantly rectilinear as in the drawings or preferably curved to offer better ergonomics. In this case, the rod 40 of the nozzle 16a is also curved to mould the cannula. The far end-cap 19 constitutes an opening through which the tubes 13 and 14 enter said body. The handpiece 10 furthermore comprises a control lever 17, means of pinching the flexible tube 13 and a device 18 for locking the control lever in the closed position in which the tube 13 is sealed and the jet of high-pressure liquid stopped.

The body is made up of two significantly identical moulded half shells 15a, one of which, the female mould, is shown by FIGS. 3A and 3B. The female mould differs from the male mould in that there are no clip-on assembly pins and in that there are housings 20 designed to receive these pins. The two half shells are hollow on the inside to allow the tubes 13 and 14 to pass inside the body of the handpiece from the far end-cap 19 to the near end-cap 16 along a significantly rectilinear path.

The control lever 17 presents a generally rectangular shape and comprises a significantly plane or inwardly curved supporting area 17' designed to receive the user's fingers or palm. It is located in the area extending from said body 14 and articulated on a pivot 21 engaged in an opening 22 in the half shells of the handpiece's body in an area close to the near end-cap. This pivot is in fact comprised of two symmetrical elements each of which is secured to a lug 23, both lugs being arranged parallel to one another. These lugs 23 provide a passage 24 for the high-pressure physiological salt solution supply tube 13. In the area extending from this passage there is a movable squeezing projection 25 secured to the control lever 17, this movable squeezing projection 25 being positioned facing a fixed squeezing projection 26 secured to the body of the handpiece and designed to cooperate with the latter to squash the tube 13, when the user presses the control lever 17 and instantaneously stop the flow of high-pressure liquid. More precisely, the squeezing projections 25, 26 define between them a space for the tube to pass 13 and they are arranged perpendicular to the latter. The movable squeezing projection 25 is designed to move in relation to the fixed squeezing projection 26 so as to reduce said space until it is cancelled thus ensuring that said tube 13 is fully squashed in a direction which is significantly perpendicular to the latter. The free end of the control lever 17 defines with the pivot 21 a lever arm D1. The ratio of the lever arms is at least between 4 and 6 and the movable squeezing projection 25 defines with said pivot 21 a lever arm D2 much smaller than D1. In the example illustrated, the ratio of the lever arms D1, D2 is close to 5. As a result, the operating force to be applied on the control lever 17 is divided by five. This original construction makes it possible to compress the tube 13 to a greater or lesser extent, even with a very high pressure, by operating the lever with your fingers easily, flexibly and without a big effort being required.

The locking means 18 are primarily comprised of a flexible tongue 27 secured to the body 15 of the handpiece and located in a significantly perpendicular plane to the free end of the control lever 17. This tongue bears a catch pin 28 close to its upper end which is fitted with a pusher 29. The catch pin 28 is designed to cooperate with a grip 30 secured to the control lever 17, when the user presses said control lever hard enough to cause the flow of high-pressure physiological salt solution to stop by pinching the flexible tube 13. In order to release the lever 17, the user acts on the pusher 29, using his thumb, which has the effect of releasing the grip from the pin 28. The flexibility of the flexible tube 13 and the pressure of the physiological salt solution conveyed by this tube bring the control lever 17 back to its initial position in which the tube 13 is fully open.

The grip 30 occupies the central position between two tabs 31 each of which has a tip 32. The tips 32 are designed to cooperate with the catch pin 28 of the flexible tongue 27 to define a position locking the control lever 17 open, as shown by FIG. 5B and in which the tube 13 is completely open.

As is shown more precisely in FIGS. 5A and 5B, the handpiece has two positions, a closing position (FIG. 5A) and an opening position (FIG. 5B). In the closing position, the grip 30 secured to the control lever 17 is stopped by the catch pin 28. The lever is pressed and the tube 13 is blocked by pinching it between the squeezing projection 25 and the fixed stop 26. In the opening position (FIG. 5B), the tips 32 secured to the tabs 31 are stopped by the catch pin 28. The lever 17 is raised and the tube is released to allow the high-pressure liquid to pass. Between these two positions, the lever 17 can be placed in an intermediate position in which the tube 13 is blocked whereas the lever 17 is not locked by the tongue 27. This intermediate position makes it possible to momentarily cut off the flow of high-pressure liquid whilst maintaining the suction.

Figure 6:
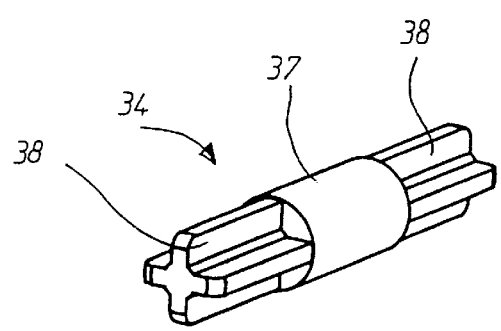
FIG. 6 shows a sealing element of the suction cannula.

On the side of the handpiece 10 there is a lateral opening 33 which corresponds to a crossing channel in which is housed a seal 34 shown in FIG. 6. The channel opens into a chamber 35 connected to the end 36 of the suction tube 14 connected to a vacuum pump. The seal 34 is designed to slide inside the crossing channel and on either side of a cylindrical central part 37 it has two grooved lateral wings 38 forming with either of the lateral openings 33 communication orifices between said suction chamber 35 and the outside environment of the handpiece. The total length of the seal 34 is greater than the width of the handpiece so that the surgeon can choose to seal either lateral opening 33 by making the seal 34 slide inside said channel crossing the body of the handpiece. When the surgeon seals one of the openings 33, using his left forefinger, if he is left-handed, or the right one if he is right-handed, the tube 14 is connected to the suction cannula 16b through the chamber 35. If the surgeon takes his forefinger off the opening 33, the suction effect at the suction cannula stops, the suction being carried out through the opening 33. This seal makes the handpiece universal, suited to both right- and left-handed users.

When using it, the handpiece 10 can be easily held and operated in one hand. The body 15 of this piece has two concave sides which give it an ergonomic profile adapted to the surgeon's fingers. The control lever 17 can be handled flexibly using the fingers. The same goes for the locking device 18. Its design is simple and its construction makes it an inexpensive component to manufacture, such that it can be considered and used as a piece to be used once only.

In actual practice, the handpiece 10 and the tubes 13 and 14 are packaged in a sterilized bag. The other sterilized and disposable parts required to use the surgical dissection instrument described, such as the pocket of physiological salt solution and the perfusion set linking said pocket to the tube 13 of the handpiece, are also packaged in individual sterilized bags.

It goes without saying that this principle of suction and of stopping the suction could also be implemented with a single lateral opening 33 provided in the body of the handpiece. In this case, the seal 34 is no longer necessary.

The present invention is not restricted to the forms of embodiment described, but can undergo various alterations and be presented in various aspects derived from the forms described in an obvious manner for an expert.

I claim:

1. A surgical dissection instrument having a pressure jet of liquid, the instrument comprising:
    a handpiece being provided with a mechanism for generating and controlling the -pressure jet of liquid, with the liquid comprising a physiological salt solution;
    a device for supplying said handpiece with the pressure jet of liquid, said handpiece (10) being provided with a hollow generally elongate body (15), said hollow body extending from a first end cap (16) to a remote second end cap (19) with both the first and second end caps being located substantially along a longitudinal axis;
    said device for supplying the handpiece (10) comprising a flexible tube (13) being housed in said body (15) and extending from the second end cap (19) to the first end cap (16) in a substantially rectilinear manner, and said flexible tube (13) being designed to withstand a pressure of at least 40 to 70 bar;
    the first end cap (16) comprising a nozzle (16a) for controlling said pressure jet of liquid; pinching mechanism for locally squashing said flexible tube (13) and restricting said pressure jet of liquid, said pinching mechanism being located in an area adjacent the first end cap (16) and comprising:
        a fixed squeezing projection (26) being secured to said body (15), the fixed squeezing projection (26) supporting said flexible tube (13) and being arranged perpendicular to said flexible tube;
        a movable squeezing projection (25) being arranged opposite said fixed squeezing projection (26), on a second side of and perpendicular to said flexible tube (13), and the fixed squeezing projection (26) and the moveable squeezing projection (25) 26) defining there between a space for said flexible tube (13) to pass, the movable squeezing projection (25) moving in relation to the fixed squeezing projection (26) so as to diminish said space and cause said flexible tube (13) to be squashed in a direction substantially perpendicular to the fixed projection;
    a lever (17) for controlling said pinching mechanism, the lever being hand-operatable by a user, the lever being mounted in a corresponding recess located in said body (15) and articulating about a pivot located between the first end cap (16) and the fixed squeezing projection (25);
    a locking mechanism (18) being combined with the control lever (17), said locking mechanism having a lower locked position for locking said control lever (17), squashing said flexible tube (13) between the moveable and fixed projections (25, 26) and a flow of the pressure jet of liquid is shut off; and
    said locking mechanism further having an unlocked position to release said control lever which moves to an upper position, under an effect of the pressure jet of liquid surging through the tube (13).

2. The instrument according to claim 1, wherein said handpiece (10) is made from an injection moulded thermoplastic synthetic material and said hollow body (15) is made from two half shells (15a) assembled together.

3. The instrument according to claim 2, wherein said control lever (17) is articulated about a pivot (21) is engaged in an opening (22) in one of said half shells (15a) of the body of the handpiece, and, depending upon a position of said control lever (17), the space defined between the fixed and movable squeezing projections (25, 26) is one of restricted and opened.

4. The instrument according to claim 3, wherein a free end of said control lever (17) defines a first lever arm about said pivot (21) and said movable squeezing projection (25) defines, with the pivot (21), a smaller second lever arm, and a ratio of the first lever arm to the second lever arm being at least 4 to 6.

5. The instrument according to claim 1, wherein said control lever (17) has a general rectangular shape and comprises one of a substantially flat supporting area and an inwardly curved supporting area (17') to receive one of a finger or a palm of a user.

6. The instrument according to claim 1, wherein the locking mechanism (18) comprises a flexible tongue (27) having a catch pin (28), the flexible tongue secured to the body (15) and cooperating with a grip (30) which is secured to the control lever (17).

7. The instrument according to claim 6, wherein said flexible tongue (27) comprises a pusher (29) located on an upper end, and said pusher is arranged to release said control lever (17) from cooperation with said flexible tongue.

8. The instrument according to claim 1, wherein said instrument further comprises a suction device (12) which has a second flexible tube (14) which extends through said handpiece (10) and a suction tube (16b) is mounted in the first end cap (16).

9. The instrument according to claim 8, wherein the handpiece (10) further comprises a chamber (35) located between an end (36) of the second flexible tube (14) and the suction tube (16b) and at least one lateral opening (33) is provided in a wall of the handpiece which joins with said chamber (35).

10. The instrument according to claim 9, wherein the handpiece (10) further comprises two lateral openings (33) which correspond to a central channel which partially crosses said chamber (35), and a seal (34) sealing at least one of said lateral openings (33).

11. The instrument according to claim 10, wherein the seal (34) has a cylindrical central part (37) and two grooved lateral wings (38), and the seal has a length greater that a width of said handpiece.

12. The instrument according to claim 8, wherein the nozzle (16a) and the suction tube (16b) are encompassed by a protective cannula (42) mounted on the first end cap (16).

* * * * *